US012667608B2

(12) United States Patent
Zhang et al.

(10) Patent No.: US 12,667,608 B2
(45) Date of Patent: Jun. 30, 2026

(54) **CONSTRUCTION METHOD OF RECOMBINANT DRUG-RESISTANT *MYCOBACTERIUM BOVIS* BACILLUS CALMETTE-GUERIN (BCG) STRAIN AND PHARMACEUTICAL COMPOSITION FOR TREATING TUBERCULOSIS (TB)**

(71) Applicant: Guangzhou Institutes of Biomedicine and Health, Chinese Academy of Sciences, Guangzhou (CN)

(72) Inventors: Tianyu Zhang, Guangzhou (CN); Bangxing Wang, Guangzhou (CN); Julius Ndirangu Mugweru, Guangzhou (CN); Gift Chiwala, Guangzhou (CN); Zhiyong Liu, Guangzhou (CN)

(73) Assignee: Guangzhou Institutes of Biomedicine and Health, Chinese Academy of Sciences, Guangzhou (CN)

( * ) Notice: Subject to any disclaimer, the term of this patent is extended or adjusted under 35 U.S.C. 154(b) by 911 days.

(21) Appl. No.: 17/886,480

(22) Filed: Aug. 12, 2022

(65) Prior Publication Data

US 2022/0387575 A1     Dec. 8, 2022

Related U.S. Application Data

(63) Continuation-in-part of application No. PCT/CN2021/076989, filed on Feb. 20, 2021.

(30) Foreign Application Priority Data

Feb. 28, 2020    (CN) .......................... 202010134454.3

(51) Int. Cl.
| | |
|---|---|
| *A61K 39/04* | (2006.01) |
| *A61K 39/00* | (2006.01) |
| *A61P 31/06* | (2006.01) |
| *C12N 15/74* | (2006.01) |

(52) U.S. Cl.
CPC .............. *A61K 39/04* (2013.01); *A61P 31/06* (2018.01); *C12N 15/74* (2013.01); *A61K 2039/52* (2013.01)

(58) Field of Classification Search
CPC ........................... C12R 2001/32; A61K 39/04; A61K 2039/52; A61P 31/06; C12N 15/74
See application file for complete search history.

(56) References Cited

FOREIGN PATENT DOCUMENTS

| | | |
|---|---|---|
| CN | 1884552 A | 12/2006 |
| CN | 102719471 B | 10/2013 |
| CN | 108823232 A | 11/2018 |

OTHER PUBLICATIONS

Danchuk et al. (2019). "Bacillus Calmette-Guerin strains with defined resistance mutations: a new tool for tuberculosis laboratory quality control". Clin. Microbiol. Infect., 26(3):384.e5-384.e8. (Year: 2019).*

(Continued)

*Primary Examiner* — Bao-Thuy L Nguyen
*Assistant Examiner* — Bailey M Morgan

(57) ABSTRACT

Disclosed are a construction method of a recombinant drug-resistant *Mycobacterium bovis* (*M. bovis*) *Bacillus* Calmette-Guerin (BCG) strain and a pharmaceutical composition for treating tuberculosis (TB). The construction method includes: using BCG as an original bacterial strain to construct a drug-resistant BCG strain resistant to at least one selected from the group consisting of STR, LFX, EMB, PRO, PAS, and AMK; and further inserting sequence fragments that can express related antigens Ag85b and Rv2628 causing an immune response into a genome of the strain to construct a recombinant drug-resistant BCG strain. The recombinant drug-resistant BCG strain can compete with *Mycobacterium tuberculosis* (Mtb) for growth, thereby accelerating the death of Mtb. When used in combination with a drug for treating TB, the recombinant drug-resistant (Continued)

BCG strain can further enhance a therapeutic effect for Mtb, and can also avoid re-infection of a patient.

7 Claims, 8 Drawing Sheets

Specification includes a Sequence Listing.

(56) References Cited

OTHER PUBLICATIONS

GenBank. (2000). "GenBank: S79283.1 ribosomal operon: ribosomal protein S12, ribosomal protein S7 [*Mycobacterium bovis*, BCG , Genomic DNA, 845 nt]" as obtained online at ncbi.nlm.nih. gov [retrieved on Oct. 7, 2025]. Retrieved from the internet: https://www.ncbi.nlm.nih.gov/nuccore/S79283 (Year: 2000).*

Fei Zhao, New Mechanisms of Para-Aminosalicylic Acid (PAS) Resistance in *Mycobacterium tuberculosis*, Medicine & Public Health of China Dotoral Dissertations Full-text Database, Jan. 15, 2015.

Yuelan Yin et al., Immunological characteristics of *Mycobacterium tuberculosis* antigen Rv2628, Chinese Journal of Biotechnology, Feb. 25, 2014, pp. 255-264, vol. 30, No. 2.

Longchang YE et al., Study on ultra-short course treatment of pulmonary *tuberculosis* with anti-tuberculosis drugs combined with Bacille Calmette-Guérin (BCG), Acta Academiae Medicinae Suzhou, Dec. 31, 1994, pp. 33-36, vol. 14, No. 1.

* cited by examiner

CONSTRUCTION METHOD OF RECOMBINANT DRUG-RESISTANT *MYCOBACTERIUM BOVIS* BACILLUS CALMETTE-GUERIN (BCG) STRAIN AND PHARMACEUTICAL COMPOSITION FOR TREATING TUBERCULOSIS (TB)

CROSS-REFERENCE TO RELATED APPLICATIONS

The present application is a continuation-in-part application of PCT application No. PCT/CN2021/076989 filed on Feb. 20, 2021, which claims the benefit of Chinese Patent Application No. 202010134454.3 filed on Feb. 28, 2020, each of which is incorporated by reference herein in its entirety.

TECHNICAL FIELD

The present disclosure belongs to the fields of genetic engineering and new vaccine development, and relates to a *Mycobacterium bovis Bacillus* Calmette-Guerin (BCG) strain and in particular to a construction method of a recombinant drug-resistant BCG strain and a pharmaceutical composition for treating tuberculosis (TB).

REFERENCE TO SEQUENCE LISTING

The Sequence Listing XML file submitted via the USPTO Patent Center, with a file name of "Sequence listing.XML", a creation date of Aug. 12, 2022, and a size of 41,660 bytes, is part of the specification and is incorporated in its entirety by reference herein.

BACKGROUND

TB, also known as phthisis and "white plague", is an ancient and protracted infectious disease, and is one of the serious diseases that endanger the human health for a long time. TB is a chronic infectious disease caused by *Mycobacterium tuberculosis* (Mtb) infection, which is a pathogen causing TB. Mtb can invade various organs of the human body, and invades the lung most often. About one third of the global population is infected with Mtb, and about 1.5 million people die from TB each year, with an average of more than 4,000 deaths per day.

In recent years, due to the dual infection of human immunodeficiency virus (HIV) and Mtb and the prevalence of drug-resistant Mtb, the incidence and mortality of TB have risen sharply, making the situation more severe. The United Nations has listed TB as one of the three major diseases to be controlled in the 21st century. TB can be cured, but requires a relatively long treatment cycle. TB caused by drug-susceptible Mtb requires a standard treatment course of 6 months, during which the 4 first-line drugs of INH, RIF, PZA, and EMB are administered during the first two months, and then INH and RIF are administered for another two months. The emergence of multidrug-resistant (MDR), extensively drug-resistant (XDR), and totally drug-resistant (TDR) TB strains makes the prevention and treatment of TB face greater challenges. The MDR strain is resistant to the two most effective drugs INH and RIF, the XDR strain is resistant to INH, RIF, at least one quinolone, and one second-line injectable drug, and the TDR strain can be resistant to more drugs. To treat patients infected with the MDR strain, a treatment course needs to be extended to 9 to 24 months and a number of drugs administered also needs to be increased to 5 to 8, but a cure rate is reduced to less than 50%. The treatment of patients infected with the XDR and TDR strains requires an extended treatment cycle and has a reduced cure rate. After TB is treated for about two months, the number of bacteria in the body is reduced to be about 10,000 to 100,000; if the drug administration is stopped, the number of bacteria will rebound immediately; and after the rebound, a treatment with the same drug is still effective, in which case Mtb does not become resistant to the drug due to genomic mutations and are merely in a state similar to dormant infection. Such a state is called a persistence state, and such bacteria are called persistence bacteria.

BCG (*Mycobacterium bovis* (*M. bovis*) BCG) is the only vaccine that can prevent TB. Although having been widely used in the world for over 100 years, BCG exhibits an unstable protective effect (0% to 80%), is almost ineffective for adults, and cannot exert a therapeutic effect for infected patients. However, an immunization effect of BCG in the body continues to weaken with age, and even if BCG is vaccinated once again in the adulthood, the effect of preventing TB cannot be achieved. BCG is susceptible to anti-TB drugs and thus is easily cleared by anti-TB drugs like Mtb, which is the most obvious defect. Therefore, when used as a therapeutic TB vaccine (for TB patients), BCG is killed. So it is difficult for BCG to play an immunoprotective role and is difficult to compete with Mtb from the perspective of microecology. In addition, the common recombinant BCG is mainly obtained by introducing an abundantly-expressed antigen protein which ignores an antigen expressed when Mtb enters a quiescent stage (a metabolically-inactive state). A therapeutic TB vaccine can be used in combination with an existing drug to shorten a TB treatment course. There are currently the following two main therapeutic TB vaccines: RUTI vaccine, which is mainly obtained by detoxifying inactivated Mtb fragments and then constructing resulting fragments in a liposome and can be used to treat latent TB infection; and SRL-172 vaccine, which is composed of heat-inactivated *Mycobacterium vaccae* (*M. vaccae*) or purified proteins from *M. vaccae* and can be used for adjuvant treatment of Mtb patients. These two therapeutic vaccines have a common disadvantage that they cannot induce sustained immunity and microecological protection after treatment.

There is an urgent need for a therapeutic vaccine with a novel action mechanism that can shorten a treatment cycle and is effective for TB caused especially by drug-resistant Mtb. A drug-resistant recombinant BCG vaccine prepared based on the combination of microecological competition theory, immunotherapy, and chemotherapy is very promising for the treatment of patients infected with drug-resistant Mtb.

SUMMARY

In view of the above problems, the present disclosure is intended to provide a therapeutic vaccine that can shorten a treatment cycle and is effective for TB caused by drug-resistant Mtb, and a pharmaceutical composition for treating TB.

To achieve the above objective, the present disclosure adopts the following technical solutions: A drug-resistant BCG strain is provided, where the drug-resistant BCG strain is a mutant strain of *M. bovis* BCG, and the drug-resistant BCG strain includes at least one selected from the group consisting of the following gene mutations: 660G>A (the numbering starts from the first nucleotide of a start codon that is numbered 1, and "G>A" means that a nucleotide G at this position is mutated into a nucleotide A; and the following gene mutations are numbered and expressed in the same way) of embB gene, 417A>G or 216C>T of embC gene, 145G>A or 228T>C or 447A>C or 483C>T of Rv3806c gene, 128G>A of rpsL gene, 192delG of rrs gene, 448C>A of eis gene, 262G>A or 263G>A of gyrA gene, and 63T>C of ethA gene.

As a preferred embodiment of the present disclosure, the drug-resistant BCG strain may be a mutant strain of *M. bovis* BCG, and the drug-resistant BCG strain may include the following gene mutations: 660G>A of embB gene, 417A>G or 216C>T of embC gene, 145G>A or 228T>C or 447A>C or 483C>T of Rv3806c gene, 128G>A of rpsL gene, 192delG of rrs gene ("del" represents "deletion"), 448C>A of eis gene, 262G>A or 263G>A of gyrA gene, and 63T>C of ethA gene.

Preferably, the drug-resistant BCG strain may be named as drug-resistant BCG, and was deposited in the Guangdong Microbial Culture Collection Center (GDMCC) located at Guangdong Institute of Microbiology, No. 100 Xianlie Middle Road Guangzhou, China (on Feb. 28, 2020), with an accession number of GDMCC 60969.

The present disclosure also provides a method for preparing a TB vaccine with the drug-resistant BCG strain.

Further, the present disclosure also provides a construction method of a recombinant drug-resistant BCG strain, including transforming a plasmid carrying sequences of Mtb-identifying protein-associated genes into the drug-resistant BCG strain described above.

As a preferred embodiment of the present disclosure, the Mtb-identifying protein-associated genes may be genes Ag85b and Rv2628.

The genes Ag85b and Rv2628 can express related antigens in an active stage and a latent stage respectively, and can provide immune protection in different growth phases of Mtb, thereby improving a protective effect of the vaccine.

The present disclosure also provides a recombinant drug-resistant BCG strain obtained according to the method described above.

Further, the recombinant drug-resistant BCG strain can be used to prepare a pharmaceutical composition for treating TB, and the pharmaceutical composition includes the recombinant drug-resistant BCG strain.

The recombinant drug-resistant BCG strain can compete with Mtb for growth, thereby accelerating the death of Mtb. When used in combination with a drug for treating TB, the recombinant drug-resistant BCG strain can further enhance a therapeutic effect for Mtb (drug-resistant Mtb), and can also avoid re-infection of a patient, which has promising medical prospects.

As a preferred embodiment of the present disclosure, the pharmaceutical composition may further include at least one selected from the group consisting of ethambutol (EMB), levofloxacin (LFX), prothionamide (PRO), and amikacin (AMK).

As a preferred embodiment of the present disclosure, the pharmaceutical composition may further include EMB, LFX, PRO, and AMK.

The present disclosure provides a drug-resistant BCG strain that can be used in combination with a chemical drug. As a therapeutic vaccine, the drug-resistant BCG strain will not be affected by a drug for treating TB, and thus can survive in the human body and compete with the disease-causing Mtb for growth, thereby accelerating the death of Mtb. The drug-resistant BCG strain can be further modified to obtain a recombinant drug-resistant BCG strain, and the recombinant drug-resistant BCG strain can be used to treat patients infected with Mtb and especially MDR Mtb, which can produce antigens against Mtb to cause a strong immune response. In addition, after treatment, the recombinant drug-resistant BCG strain can continue to survive in the body for a specified period of time, which helps to protect a patient and reduce a risk of re-infection.

DETAILED DESCRIPTION

Figure 1:
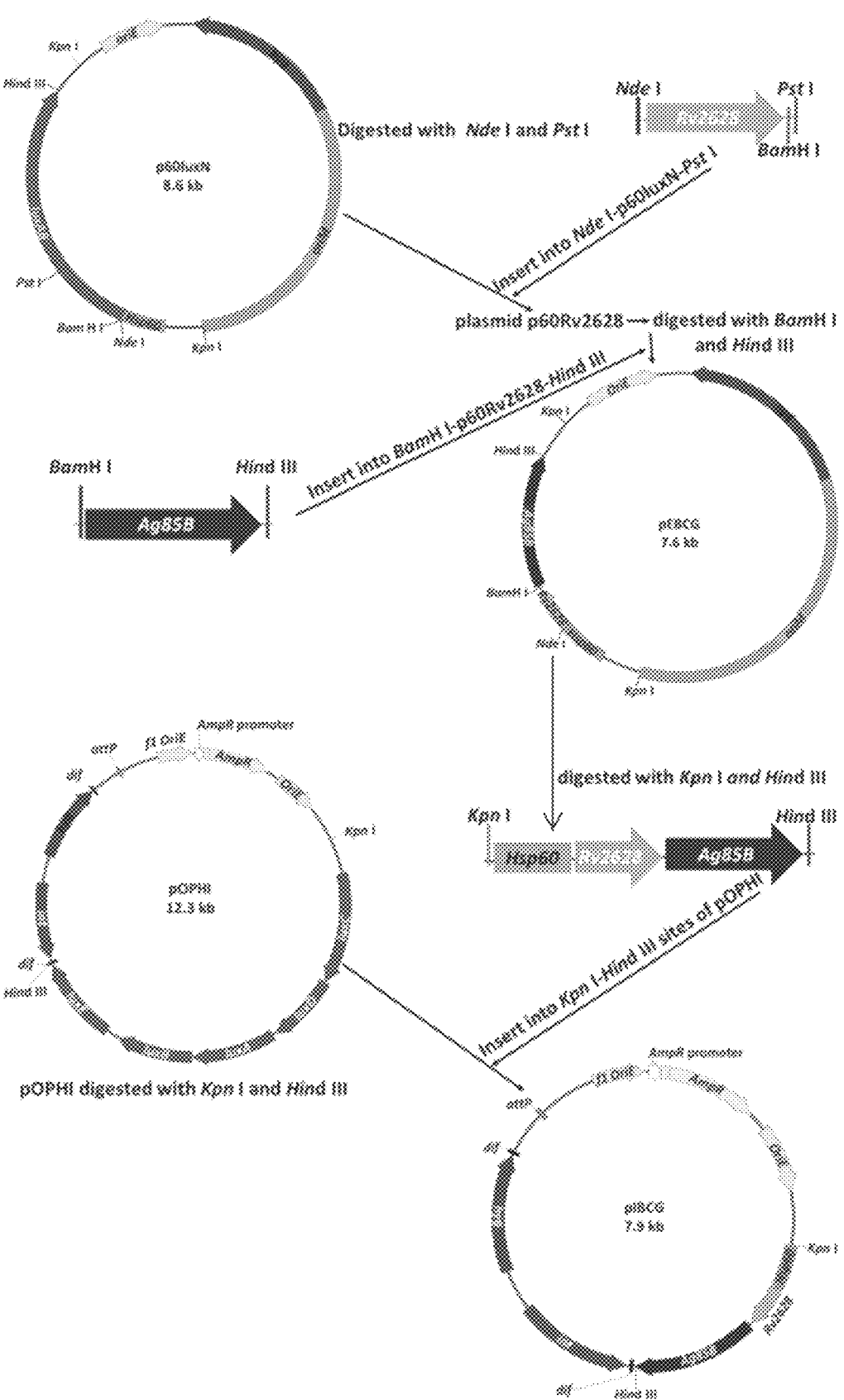
FIG. 1 is a construction flow chart of the plasmid pIBCG, wherein Rv2628 was amplified from *M. tuberculosis* which was digested with Nde I and Pst I, Ag85B was amplified from *M. tuberculosis* which was digested with BamH I and Hind III, and Hsp60-Rv2628-Ag85B was excised from pEBCG which was digested with Kpn I and Hind III.

To better explain the objectives, technical solutions, and advantages of the present disclosure, the present disclosure will be further explained below with reference to accompanying drawings and specific examples.

Example 1 Construction Method of a Drug-Resistant BCG Strain

I. Preparation of 7H9 and 7H11 Culture Media 1. 7H9 liquid culture medium: 4.7 g of 7H9 powder, 2 mL of glycerol, and 900 mL of ddH$_2$O were mixed, sterilized at a high temperature and a high pressure, and then cooled, and 100 mL of OADC was added; and 2. 7H11 solid culture medium: 19 g of 7H11 powder, 5 mL of glycerol, and 900 mL of ddH$_2$O were mixed, sterilized at a high temperature and a high pressure, and then cooled, and 100 mL of OADC was added.

II. Screening of Spontaneously Drug-Resistant BCG

1. With a minimal inhibitory concentration (MIC) of *M. bovis* BCG (hereinafter referred to as wild-type (WT) BCG, which was provided by Johns Hopkins University School of Medicine) for streptomycin (STR) being 0.25 pg/mL, a streptomycin (STR)-containing 7H11 plate (with a final concentration of 0.25*MIC-8*MIC) and a 7H11 blank plate were prepared. *M. bovis* BCG at a logarithmic growth phase was taken and diluted to an appropriate concentration, then 500 μL of a resulting bacterial suspension was pipetted and evenly spread on the plates. The plates were incubated in a constant-temperature incubator for four weeks. Then the colony count was conducted, and MIC was calculated. This method was used to detect the MIC of *M. bovis* BCG for STR, LFX, EMB, PRO, para-aminosalicylic acid (PAS), and AMK.

and AMK) according to the method in 2, then single colonies were picked and cultivated in a 50 mL centrifuge tube with the 7H9 culture medium, and identification was conducted to finally obtain a BCG strain resistant to STR, LFX, EMB, PRO, PAS, and AMK (referred to as drug-resistant BCG).

Target genes and primer sequences of the above drugs were shown in Table 1.

TABLE 1

Target genes and primer sequences of drugs

| Drug | Primer pair | Primer sequence (5'-3') | Product length (bp) |
|---|---|---|---|
| EMB | embCF/embCR | CCCAATGTTCGCCGCTAC (SEQ ID NO: 1) ACGAGGCTCGATGGTAGG (SEQ ID NO: 2) | 3491 |
| | Rv3795F/Rv3795R | GGGATCGGTGGAGCAGTA (SEQ ID NO: 3) ACCGAGCAGCATAGGAGG (SEQ ID NO: 4) | 3496 |
| | Rv3806cF/Rv3806cR | GATGTGGCCGTGGGTGTT (SEQ ID NO: 5) CGTCACCGACAGCCACAA (SEQ ID NO: 6) | 1126 |
| PRO | EthRF/EthRR | TTTTCCAGGATGGCGTAGC (SEQ ID NO: 7) CCGACCGGATCGTCAACA (SEQ ID NO: 8) | 1099 |
| | EthAF/EthAR | CCTGGCAGCTTACTACGTGTC (SEQ ID NO: 9) CGGCATCATCGTCGTCTG (SEQ ID NO: 10) | 1599 |
| | inhAF/inhAR | TCACGGCGGTAGAAGAGCA (SEQ ID NO: 11) CCACGCAGATGTCGCAAAGA (SEQ ID NO: 12) | 1684 |
| | KatGF/KatGR | TGCGAAAGATCCAACCCTC (SEQ ID NO: 13) AGACCAACCGTGTAGGCAAAT (SEQ ID NO: 14) | 2816 |
| | NdhF/NdhR | ACTTGGCTCCGCACGGCTAT (SEQ ID NO: 15) ATCCGGCGACGGCATTCA (SEQ ID NO: 16) | 1718 |
| | ahpCF/ahpCR | CGACTGGCTCATATCGAGAAT (SEQ ID NO: 17) AATACCTGCGGATTTCGTGT (SEQ ID NO: 18) | 984 |
| AMK | rrs F/rrs R | GCGGGCGGAAACAAGCAA (SEQ ID NO: 19) CAAGGCGGTGGGACAACA (SEQ ID NO: 20) | 1879 |
| | eisF/eisR | CCGCATCGCGTGATCCTT (SEQ ID NO: 21) CGCTGACCACGCCGAAAA (SEQ ID NO: 22) | 1343 |
| | tLyAF/tLyAR | TTTCCGAGGCGCACGAGG (SEQ ID NO: 23) CGTCGGGAGCCAGATGCA (SEQ ID NO: 24) | 1032 |
| LFX | gyrAF/gyrAR | TTCATATGACAGACACGACGTTGCC (SEQ ID NO: 25) CGCAAGCTT AATTGCCCGTCTGGTCT (SEQ ID NO: 26) | 2715 |
| | gyrBF/gyrBR | CCGTATGCCGGACGTCG (SEQ ID NO: 27) GCGGCCGACGATCAC (SEQ ID NO: 28) | 2356 |
| STR | rpsLF/rpsLR | GCGGCTTACGCCTGATGT (SEQ ID NO: 29) CAGGGCGGGTTTGACATT (SEQ ID NO: 30) | 629 |
| | RrsfF/RrsR | TATCTATGGATGACCGAACCT (SEQ ID NO: 31) TGGGACAACACCTGGAAC (SEQ ID NO: 32) | 1782 |
| PAS | thyAF/thyAR | GCCCGCTGGGTTTGTTTG (SEQ ID NO: 33) GATGACACCCGATGTCGCTTGAGCC (SEQ ID NO: 34) | 987 |
| | dfrAF/dfrAR | GGCGATCAAAGCTCCAGTC (SEQ ID NO: 35) CGAATCCAGCTACCGCACT (SEQ ID NO: 36) | 792 |
| | FoLp1F/FoLp1R | TCGTGGTGATCGAGGCTGAG (SEQ ID NO: 37) CGGCCAAGTCGTCGCTGTT (SEQ ID NO: 38) | 1128 |
| | FoLp2F/FoLp2R | GGCTATGCACTTCCGCTCTTT (SEQ ID NO: 39) TTGCCGCTTCCAACTCCC (SEQ ID NO: 40) | 1346 |

2. According to the obtained MIC value for STR, 7H11 plates with different concentrations of STR (0.5*MIC-128*MIC) and a blank 7H11 plate were prepared. BCG at a logarithmic growth phase ($OD_{600}$=0.6 to 0.8) was taken, and 500 μL of a bacterial solution was evenly spread on each plate and then cultivated in a constant-temperature incubator for 4 weeks; single colonies were picked, inoculated into a 50 mL centrifuge tube with the 7H9 culture medium, and cultivated on a shaker. After the single colonies grew to a logarithmic phase, a bacterial solution was taken for polymerase chain reaction (PCR) and sequencing to confirm an STR-resistant BCG strain obtained.

3. The STR-resistant BCG strain obtained was cultivated on 7H11 plates each with a first-line or second-line anti-TB drug (an order of screening drugs: LFX, EMB, PRO, PAS, 4. The spontaneously drug-resistant BCG finally obtained after the screening was identified and inoculated into a 50 mL centrifuge tube with the 7H9 culture medium and cultivated on a shaker; after growing to a logarithmic phase, the BCG was diluted to an appropriate concentration, and 500 μL of a resulting bacterial solution was pipetted and spread on each of 7H11 plates with a single screening drug mentioned above (drug concentration: 0.5*MIC-128*MIC) and a blank 7H11 plate, and cultivated in a constant-temperature incubator for 4 weeks; and the colony count was conducted, and then an MIC of the drug-resistant BCG strain for each screening drug was calculated. The MICs and drug resistance mechanisms of the drug-resistant BCG obtained after the sequencing to the screening drugs were shown in Table 2.

TABLE 2

MICs and drug resistance mechanisms of the spontaneously drug-resistant *M. bovis* BCG for screening drugs

| Drug | Detection concentration (μg/mL) | Gene | Nucleotide | Amino acid | Number of mutant strains |
|---|---|---|---|---|---|
| EMB | 5 | embB | CTG660CTA | Leu220Leu | 3 |
| | | embC | TTA417TTG | Leu139Leu | |
| | | embC | CTG2167TTG | Leu723Leu | |
| | | Rv3806c | GTC145ATC | Val49Ile | |
| | | Rv3806c | CGT228CGC | Arg76Arg | |
| | | Rv3806c | GAA447GAC | Glu149Asp | |
| | | Rv3806c | GCC483GCT | Ala161Ala | |
| STR | 10 | rpsL | AAA128AGA | Lys43Arg | 3 |
| AMK | 10 | rrs | AGG192AG | Deletion | 3 |
| | | eis | CCG448AGA | Arg149Arg | |
| | | tlyA | None | | |
| LFX | 2 | gyrA | GGC262AAC | Gly88Asn | 3 |
| MFX | 2 | | None | | |
| PAS | 30 | | None | | 3 |
| PRO | 30 | ethA | TGG63CGG | Trp21Arg | 1 |
| | | ethR | None | | |
| | | inhA | | | |
| | | katG | | | |
| | | ndhf | | | |
| | | ahpC | | | |

The drug-resistant BCG strain was named as drug-resistant BCG, and was deposited in the Guangdong Microbial Culture Collection Center (GDMCC) located at Guangdong Institute of Microbiology, No. 100 Xianlie Middle Road Guangzhou, China on Feb. 28, 2020, with an accession number of GDMCC 60969.

Example 2 Construction of a Recombinant Drug-Resistant BCG Strain

I. Construction of a Recombinant Plasmid Carrying Ag85b and Rv2628 Gene Fragments 1. PCR Product Recovery and Digestion A construction process of the plasmid was shown in FIG. 1. With genomic DNA (gDNA) of Mtb H37Rv (provided by the Guangzhou Chest Hospital) as a template, PCR was conducted to amplify the Ag85b (primer pair: F: 5'-CGG-GATCCATGAGACGACTTTGACGCCCGAA-3' (SEQ ID NO: 41), and R: 5'-CCCCTGCAGGGATCCTTA-GACCGCAACGGCAATCT-3' (SEQ ID NO: 42)) and Rv2628 (primer pair: F: 5'-GGAATTCCATATGATGTC-CACGCAACGACCGA-3' (SEQ ID NO: 43), and R: 5'-CCCCTGCAGGGATCCTTA-GACCGCAACGGCAATCT-3' (SEQ ID NO: 44)) gene fragments, and PCR products were subjected to 0.8% agarose gel electrophoresis, recovered, and identified by sequencing.

Figure 2:
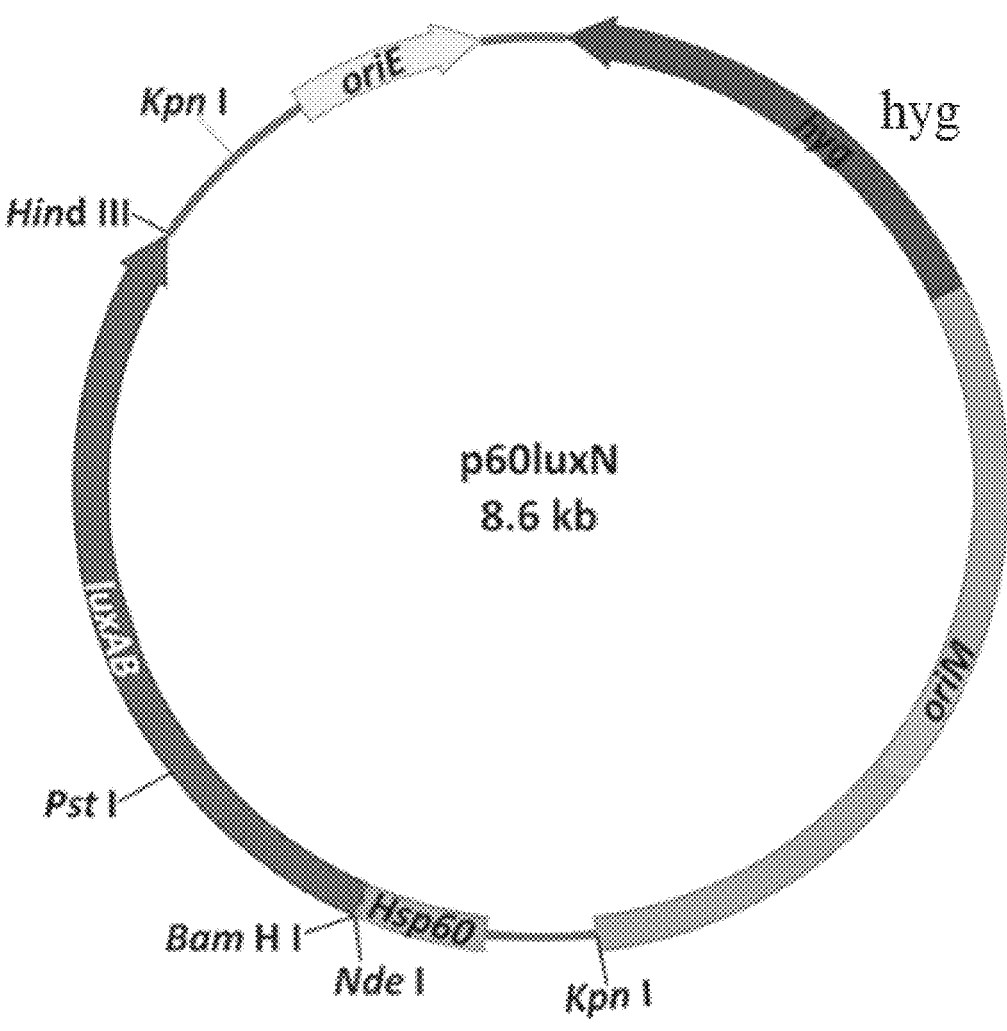
FIG. 2 is a map of the plasmid p60luxN in FIG. 1.

The recovered and identified Rv2628 fragment and the starting plasmid p60LuxN (the plasmid was constructed by the laboratory of the present disclosure, a map of the plasmid was shown in FIG. 2, and a specific construction method can be found in the relevant content of reference CN 201810359440.4) were each subjected to double digestion with restriction endonucleases Nde I and Pst I, and digestion products were recovered by the method of PCR product purification. An enzyme digestion system was shown in Table 3.

TABLE 3

| Enzyme digestion system | |
|---|---|
| DNA fragment/plasmid | 17 μL |
| 10 × K Buffer | 2 μL |
| Nde I | 0.5 μL |
| Pst I | 0.5 μL |
| Total | 20 μL |

2. Ligation and Transformation

After the digestion products were recovered, a volume ratio of gene fragments to vector fragments in an enzyme ligation system was further determined to be 3:1 through agarose gel electrophoresis comparison. The enzyme ligation system was prepared according to Table 4, and ligation was conducted overnight at 16° C.

TABLE 4

| Enzyme ligation system | |
|---|---|
| Vector fragments | 2 μL |
| Gene fragments | 6 μL |
| 10 × Ligation buffer | 1 μL |
| T4 DNA Ligase | 1 μL |
| Total | 10 μL |

A ligation product was added to 50 μL of an *Escherichia coli* (*E. coli*) DH5a competent cell solution prepared in the laboratory, and a resulting mixture was allowed to stand on ice for 30 min and then transferred to a water bath at 42° C.; then the mixture was subjected to heat shock for 90 s, and then placed on ice for 2 min; 1 mL of an LB liquid culture medium was added, the competent cells were cultivated on a shaker at 37° C. and 180 rpm/min for 1 h, and a resulting bacterial solution was centrifuged; and a resulting supernatant was removed, and resulting bacterial cells were resuspended with 800 μL of an LB liquid culture medium, spread on an LB solid culture medium (with 50 μg/mL hygromycin), and cultivated in a 37° C. incubator for 16 h.

3. Identification of the Recombinant Plasmid

The above-mentioned primers for amplifying the Rv2628 gene fragment were used to conduct PCR identification on single colonies picked from the LB plate, and single colonies identified as positive by PCR were inoculated into 5 mL of an LB culture medium and cultivated on a 37° C. shaker for 12 h to 16 h. A resulting bacterial solution was collected and subjected to plasmid extraction. An extracted plasmid was identified by double enzyme digestion with Nde I and Pst I, and if an identification result was positive, the plasmid was sent to a company for sequencing. A plasmid with a correct sequence was named as p60Rv2628.

4. The plasmid p60Rv2628 obtained and the Ag85b gene fragment amplified by PCR were subjected to digestion with BamH I and Hind III, ligation, transformation, and identification according to the above-mentioned method to obtain a plasmid carrying both the Ag85b gene fragment and the Rv2628 gene fragment, which was named as pEBCG.

Figure 3:
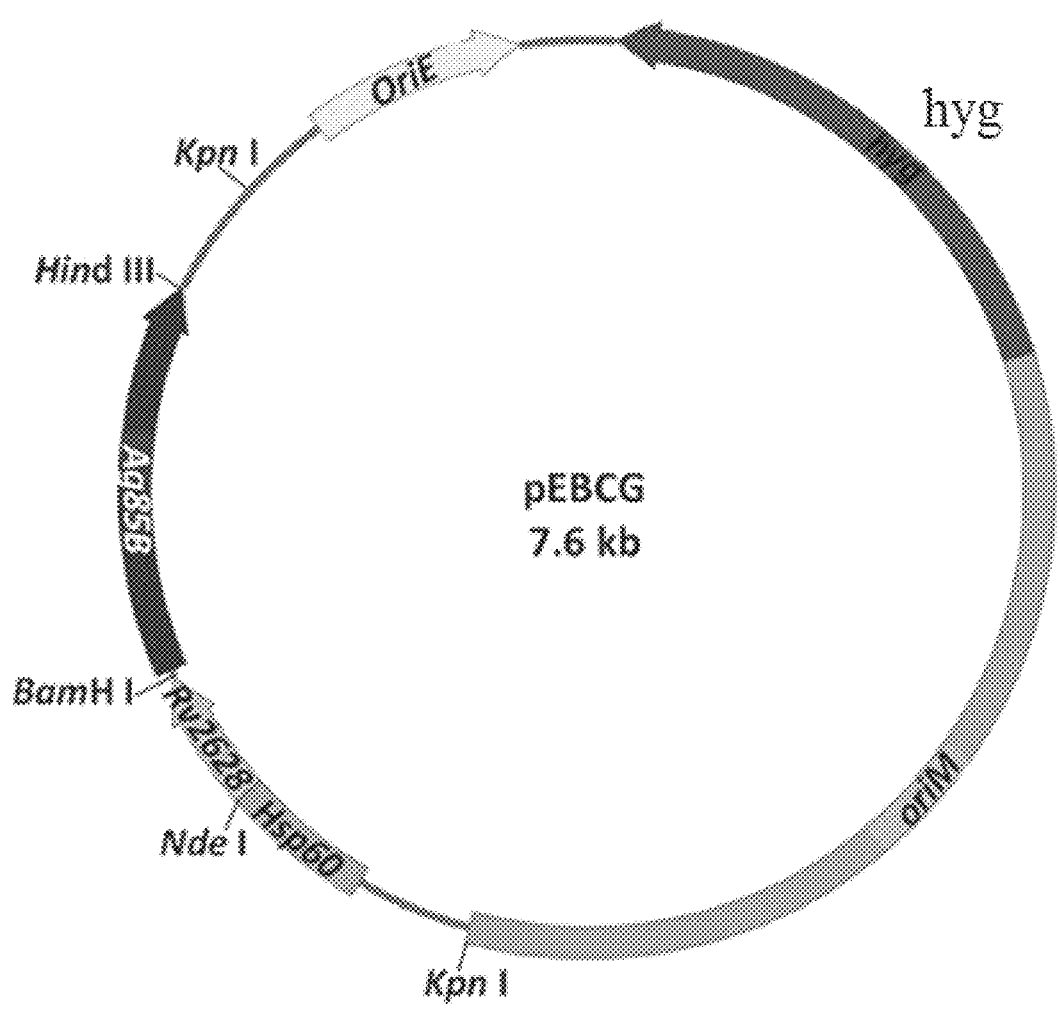
FIG. 3 is a map of the plasmid pEBCG in FIG. 1.
Figure 4:
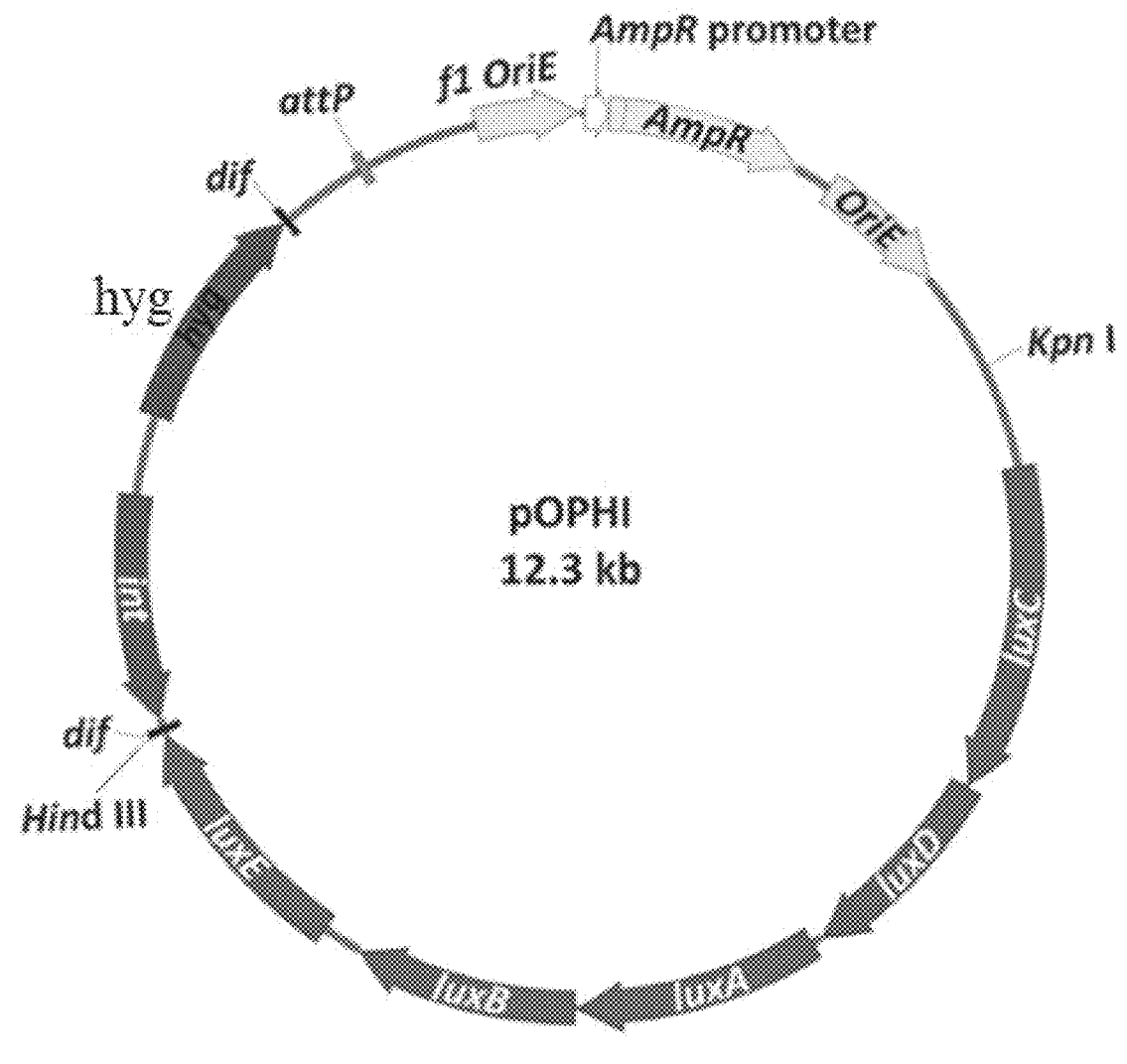
FIG. 4 is a map of the plasmid pOPHI in FIG. 1.
Figure 5:
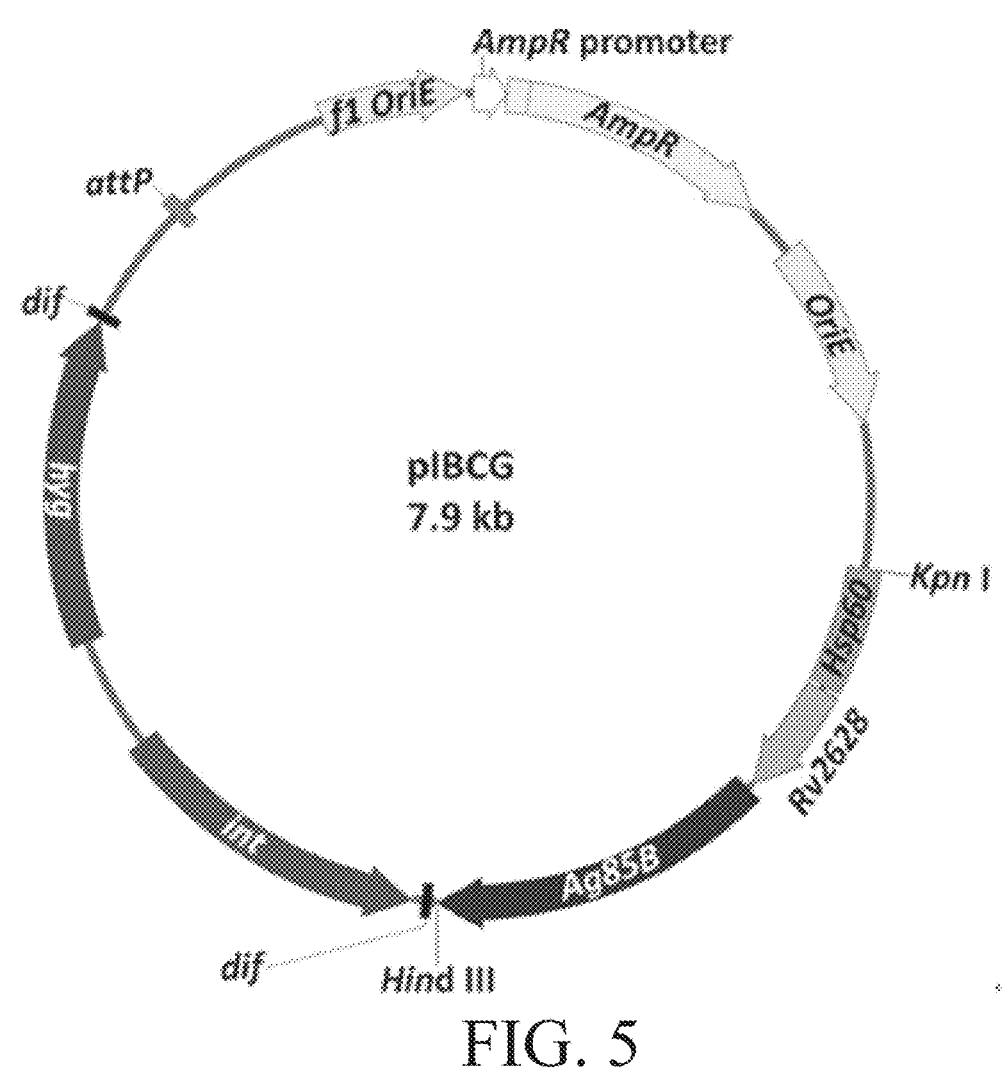
FIG. 5 is a map of the plasmid pIBCG in FIG. 1.

5. The plasmid pEBCG obtained (as shown in FIG. 3) and the plasmid pOPHI (as shown in FIG. 4, which can also be seen in Chinese Patent CN 201210183007.2) were subjected to digestion with Kpn I and Hind III, ligation, transformation, and identification according to the above-mentioned method to obtain a plasmid, which was named as pIBCG (as shown in FIG. 5).

II. Construction of a Recombinant Drug-Resistant BCG Strain

The plasmids p60LuxNC (control) and pIBCG were each electroporated into competent BCG (prepared from the drug-resistant BCG prepared in Example 1) with an electroporator at 2.5 Kv. An electroporation cuvette was rinsed with the 7H9 culture medium, a resulting bacterial solution was transferred to a 50 mL centrifuge tube, an appropriate amount of the 7H9 culture medium was added, the bacterial solution was cultivated for 20 h; then 500 μL of a resulting bacterial solution was taken and spread on a hygromycin (50 g/mL)-containing 7H11 plate, and the plate was incubated in a constant-temperature incubator at 37° C. for 4 weeks. Colonies were picked and inoculated in a 7H9 culture medium (with 10 g/mL hygromycin) and cultivated for 4 weeks. A resulting bacterial solution was serially diluted to 1,000 times, and diluted bacterial solutions were spread on hygromycin (50 g/mL)-containing and blank 7H11 plates and cultivated for 5 weeks. Single colonies on the hygromycin-containing plate were picked, subjected to expanded cultivation, and DNA extraction. A primer pair Mark-F (5'-CGATGTGGTCGGATAGGCA-3', SEQ ID NO: 45) and Mark-R (5'-ACTCACCTGCGGTTTATCTGC-3', SEQ ID NO: 46) was used for amplification and identification to obtain a 0.6 kb fragment (that is, a fragment including the Ag85B gene and the Rv2628 gene), indicating that the recombinant drug-resistant BCG strain was successfully constructed.

Example 3 Plasmid Stability Detection for the Recombinant Drug-Resistant BCG

The recombinant drug-resistant BCG obtained was diluted to an appropriate concentration, cultivated in a hygromycin-containing 7H9 culture medium, and continuously subcultured five times. Bacterial solutions of passages 4 and 5 each were serially diluted, spread on a hygromycin-containing 7H11 plate, and cultivated in an incubator for four weeks. Single colonies were picked, subjected to expanded cultivation, and DNA extraction. A primer pair Mark-F (5'-CGATGTGGTCGGATAGGCA-3', SEQ ID NO: 45) and Mark-R (5'-ACTCACCTGCGGTTTATCTGC-3', SEQ ID NO: 46) was used for amplification and identification to obtain a 0.6 kb fragment, that is, a fragment including the Ag85B gene and the Rv2628 gene.

Figure 6:
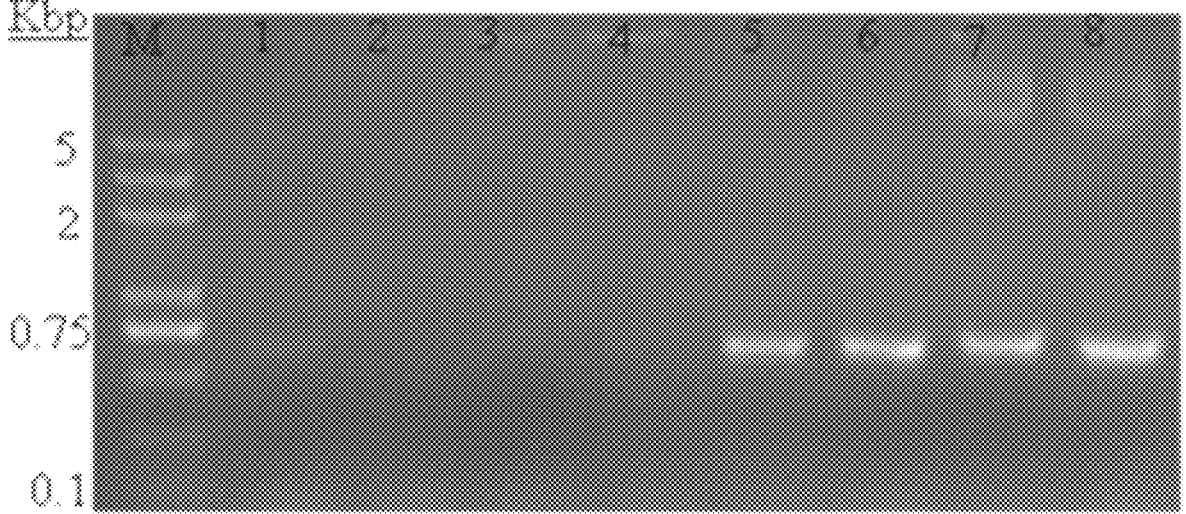
FIG. 6 is an electrophoretogram illustrating the stable expression of the plasmid of the recombinant drug-resistant BCG after subculture.

Colonies obtained after 5 consecutive times of subculture were randomly picked, and colony PCR was conducted using the above primer pair (Mark-F and Mark-R). Results were shown in FIG. 6. It can be seen from FIG. 6 that 50% of the single colonies have obvious bands in electrophoresis after PCR detection under no selection pressure, indicating that the plasmid of the recombinant drug-resistant BCG has high stability.

Example 4 Determination of MIC of the Recombinant Drug-Resistant BCG In Vitro

The recombinant drug-resistant BCG strain constructed was inoculated into a 50 mL centrifuge tube with the 7H9 culture medium, and cultivated on a shaker; after the strain grew to a logarithmic phase, a resulting bacterial solution was appropriately diluted, and 500 μL of a diluted bacterial solution was spread on a 7H11 plate with EMB, STR, AMK, LFX, moxifloxacin, PAS, PRO, clofazimine (CLA), isoniazid, rifampicin, Pretomanid (PA-824), bedaquiline (TMC207), or linezolid (LZD) and a blank 7H11 plate and cultivated in a constant-temperature incubator for 4 weeks; and the colony count was conducted, and then an MIC of the recombinant drug-resistant BCG strain for each screening drug was calculated (as shown in FIG. 5).

TABLE 5

MICs of the recombinant drug-resistant BCG for screening drugs

| | Strain/MIC (μg/mL) | | |
| --- | --- | --- | --- |
| Drug | Recombinant drug-resistant BCG Strain | *M. bovis* BCG | Mtb H37Rv |
| EMB | 5 | 0.5 | 0.5 |
| STR | 64 | 0.25 | 1 |
| AMK | 5 | 0.5 | 0.5-1 |
| LFX | 4 | 0.5 | 0.5 |
| MFX | 4 | 0.5 | 0.25-0.5 |
| PAS | 0.25 | 0.25 | 0.3-1 |
| PRO | 64 | 0.25 | 0.5 |
| CLA | 0.5 | 0.25 | 8 |
| INH | 0.06 | 0.1 | 0.03-0.06 |
| RIF | 0.5 | 0.032 | 0.25 |
| PA-824 | 0.25 | 0.25 | 0.06-0.125 |
| TMC 207 | 0.03 | 0.03 | 0.03-0.12 |
| LZD | 0.03 | 0.125-0.5 | 0.25 |

Example 5 Detection of Safety and Virulence of the Recombinant Drug-Resistant BCG Strain SCID mice each with a body weight of 14 g to 17 g were selected and adaptively raised in the laboratory for a few days, and then a WT BCG bacterial solution and a recombinant drug-resistant BCG bacterial solution with an $OD_{600}$ of 0.8 to 1.0 were taken and then each injected into 30 SCID mice through the tail vein at a dose of 200 L/mouse.

According to the type of injected bacteria, mice were randomly divided in cages, with 5 mice in each cage. After being divided into cages, the mice were raised according to the feeding standards of SCID mice. Survival statuses of the mice were observed and recorded every day and the mice in each group were weighed every week. Results were shown in FIG. 7.

On day 2 after the injection, 3 mice were taken from each group and weighed, the spleen and lung were collected, and the spleen was weighed; and the lung tissue was thoroughly ground, diluted to an appropriate concentration, spread on a 7H11 plate, and cultivated in a constant-temperature incubator for 4 weeks, and the colony count was conducted to calculate a bacterial load.

At week 2 and 4 after the injection, 5 mice were taken from each group and weighed, the spleen and lung were collected, and the spleen was weighed (results were shown in FIG. 8); and the lung tissue was thoroughly ground, diluted to an appropriate concentration, spread on a 7H11 plate, and cultivated in a constant-temperature incubator for 4 weeks, and the colony count was conducted to calculate a bacterial load. At week 20, the remaining mice in each group were treated according to the above method. Bacterial loads in the spleen and lung of each mouse were shown in FIG. 9.

Figures 7, 8:
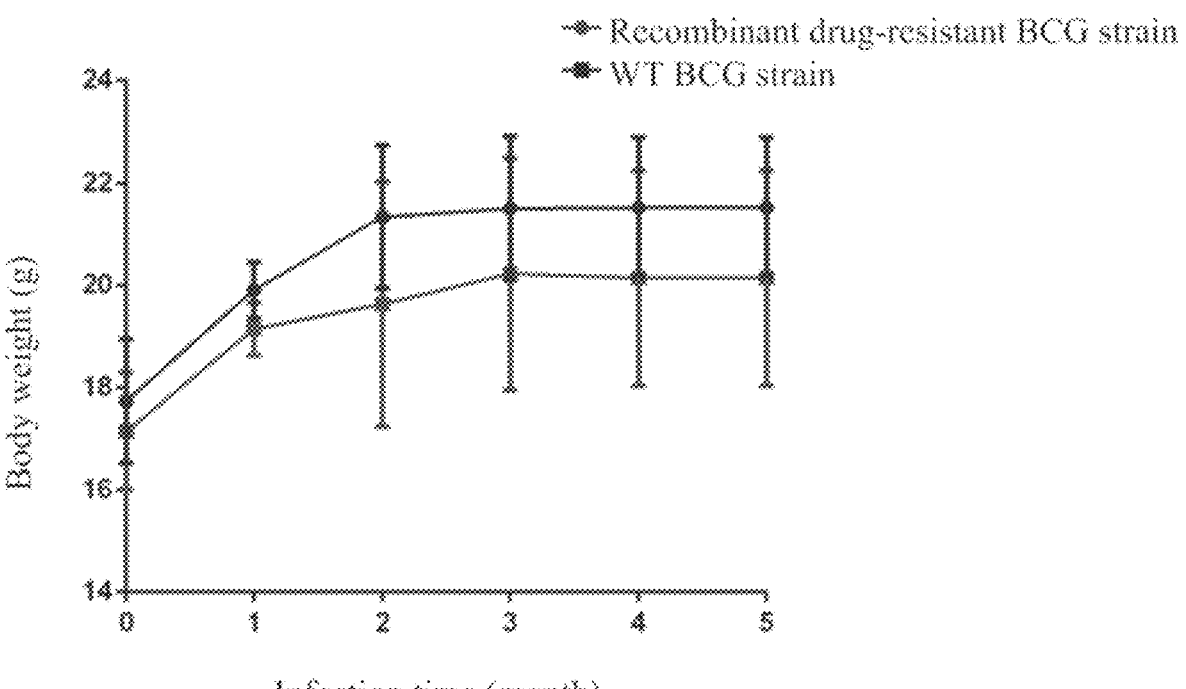
FIG. 7 shows the body weight changes of severe combined immunodeficiency (SCID) mice infected with the recombinant drug-resistant BCG.
FIG. 8 shows the spleen weight changes of SCID mice infected with the recombinant drug-resistant BCG.
Figures 9, 10:
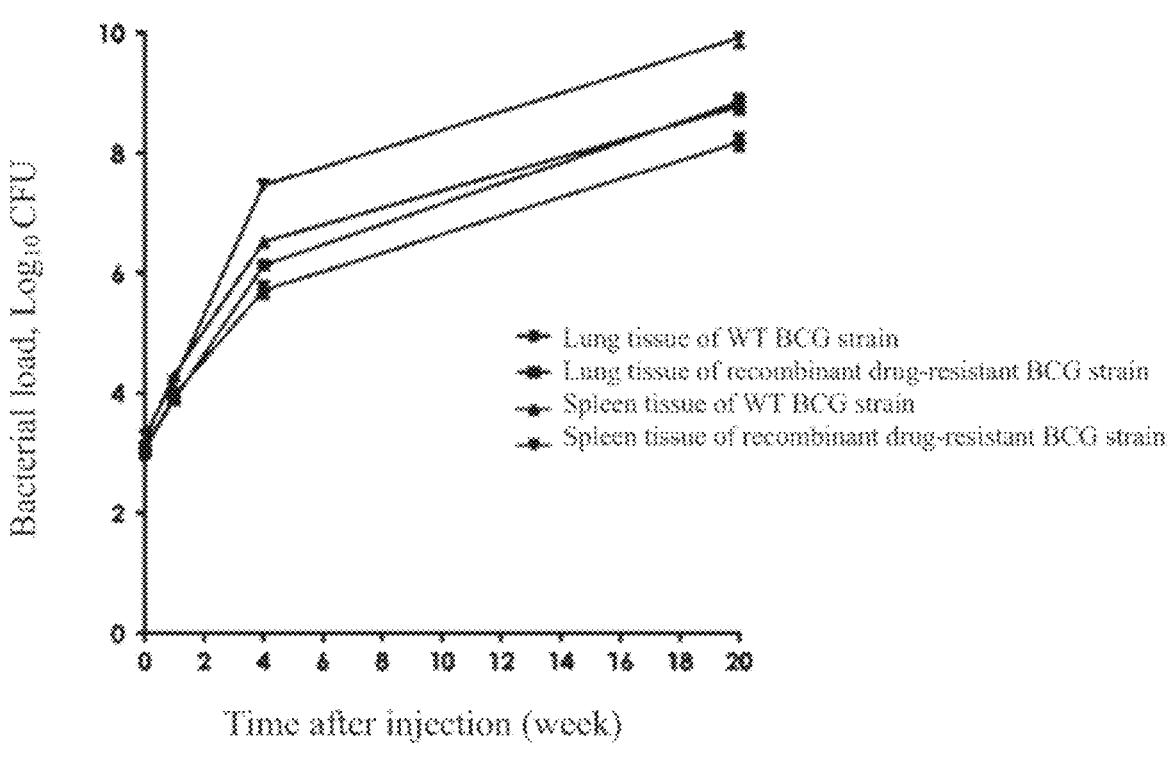
FIG. 9 shows the bacterial loads in the spleen and lung of SCID mice infected with the recombinant drug-resistant BCG.
FIG. 10 shows an inhibitory effect of the recombinant drug-resistant BCG on H37Rv when a titer of the recombinant drug-resistant BCG is higher than or close to a titer of the Mtb.

It can be seen from FIG. 7 to FIG. 9, a weight gain of the mice infected with the recombinant drug-resistant BCG bacteria was significantly lower than a weight gain of the mice infected with the WT BCG bacteria, and a spleen weight of the mice infected with the recombinant drug-resistant BCG bacteria was significantly increased, indicating that the immune system was activated; and bacterial loads in the lung and spleen tissues of mice infected with the recombinant drug-resistant BCG bacteria were significantly higher than bacterial loads in the lung and spleen tissues of mice infected with the WT BCG bacteria, indicating that the mice infected with the recombinant drug-resistant BCG exhibited a prominent immune effect.

Example 6 Inhibitory Effects of the Recombinant Drug-Resistant BCG at Different Concentrations on H37Rv In Vitro and In Vivo The autoluminescent Mtb H37Rv (ALRV) with an $OD_{600}$ of 0.8 to 1.0 and the recombinant drug-resistant BCG bacteria (rdrBCG) were each serially diluted (with a dilution gradient in Table 6), and a stock solution and diluted solutions of ALRV were each mixed with each of a stock solution and diluted solutions of rdrBCG in a 50 mL centrifuge tube according to a specified volume ratio. A mixed bacterial solution was cultivated in a constant-temperature incubator, and a relative luminescence value (RLU) was detected regularly. Results were shown in FIG. 10.

TABLE 6

| No. | Dilution instructions | Notes |
|---|---|---|
| | Dilution instructions for ALRV and rdrBCG | |
| A1 | Undiluted ALRV | Autoluminescent laboratory standard |
| AI | ALRV diluted 10 times | TB |
| A3 | ALRV diluted 100 times | |
| B1 | Undiluted rdrBCG | rdrBCG |
| B2 | rdrBCG diluted 10 times | |
| B3 | rdrBCG diluted 100 times | |
| B4 | rdrBCG diluted 1,000 times | |
| C1 | Control | Culture medium |

It can be seen from FIG. 10 that the recombinant drug-resistant BCG strain exhibited a significant inhibitory effect on the growth of the autoluminescent Mtb in vitro, and the inhibitory effect increased with the increase of BCG concentration.

Example 7 Experiment of the Recombinant Drug-Resistant BCG in Mice

1. Preparation and Validation of Rifampicin-Resistant Mtb H37Rv

An Mtb H37Rv bacterial solution with $OD_{600}$ of 0.8 to 1.0 was taken, and concentrated 10 times and 20 times. A stock solution was sequentially diluted to $10^{-4}$ and $10^{-6}$, and then 500 L of each of the stock solution, the $10^{-4}$ diluted solution, and the $10^{-6}$ diluted solution was taken and evenly spread on a 7H11 blank plate to calculate the number of Mtb in a bacterial solution. 500 μL of a concentrated solution was taken and evenly spread on 7H11 plates with different concentrations of rifampicin (4 g/mL and 10 p/mL), and then cultivated in a constant-temperature incubator; and after there were colonies, single colonies were picked and cultivated in a 50 mL centrifuge tube, and a mutation of the rifampicin resistance-related gene rpoB was detected by sequencing. A mutation (TCG-TTG) was found at position 531 (with the first nucleotide of a start codon as position 1) after sequence alignment, which was consistent with that reported in literatures.

2. Infection, Treatment, and Immunization of Mice

BALB/C mice (80 mice) each with a weight of 14 g to 17 g were adaptively raised for a few days in the P3 laboratory, then subjected to aerosol infection for 45 min through Glas-Col using rifampicin-resistant Mtb H37Rv with $OD_{600}$ of 0.8 to 1.0, and then randomly divided into cages, with 5 mice in each cage, including 15 mice for the untreated group, 25 mice for the treated group (Tt), 20 mice for the WT BCG immunotherapy group (Tt+wt), and 20 mice for the recombinant drug-resistant BCG immunotherapy group (Tt+rdr).

On day 1 and day 28 after the infection, 5 mice were taken from the untreated group and sacrificed, the lung was collected, thoroughly ground, diluted to an appropriate concentration, spread on a 7H11 plate, and cultivated in a constant-temperature incubator for 4 weeks, and the colony count was conducted to calculate a bacterial load. At other detection time points, 5 mice were sacrificed according to the experimental protocol in Table 7, and a bacterial load was detected by the same method.

The treatment was started on day 28 after the infection, where the drugs were administered once a day, 5 days a week. Early-stage treatment (two months) regimen: EMB (150 mg/kg, intragastrically), LFX (300 mg/kg, intragastrically), PRO (25 mg/kg, intragastrically), and AMK (100 mg/kg, subcutaneously); and late-stage treatment (three months) regimen: EMB (150 mg/kg, intragastrically), LFX (300 mg/kg, intragastrically), and PRO (25 mg/kg, intragastrically). After two months of treatment, aerosol infection (as) and subcutaneous injection (sc) were used for immunization. rdrBCG at a logarithmic growth phase was centrifuged, a resulting supernatant was discarded, PBS was added to resuspend, and an $OD_{600}$ value was adjusted to 0.5 for immunization. Aerosol infection immunization: Glas-Col was used to conduct aerosol infection for 45 min to achieve immunization; and subcutaneous injection immunization: 200 μL of a bacterial solution was subcutaneously injected. The subsequent immunization schedule and bacterial load detection schedule were shown in Table 7.

TABLE 7

Immunization and bacterial load detection schedules

| | | Time points/number of mice sacrificed | | | | | | | |
|---|---|---|---|---|---|---|---|---|---|
| No. | Group | Infection Day-14* | Treatment Day 0 | Treatment Week 4 | Treatment Week 8 | Treatment Week 12 | Treatment Week 16 | Treatment Week 20 | Total |
| 1 | Untreated | 5 | 5 | 5 | | | | | 15 |
| 2 | Treated | | 5 | | 5 | 5 | 5 | 5 | 25 |
| 3 | Tt + rdr(sc) | | | | Immunization | Immunization | Immunization 5 | 5 | 10 |
| 4 | Tt + wt (sc) | | | | Immunization | Immunization | Immunization 5 | 5 | 10 |
| 5 | Tt + rdr (as) | | | | Immunization | Immunization | Immunization 5 | 5 | 10 |
| 6 | Tt + wt (as) | | | | Immunization | Immunization | Immunization 5 | 5 | 10 |
| Total | | 5 | 5 | 10 | 5 | 5 | 25 | 25 | 80 |

*The day after infection, five mice were sacrificed.

Figure 11:
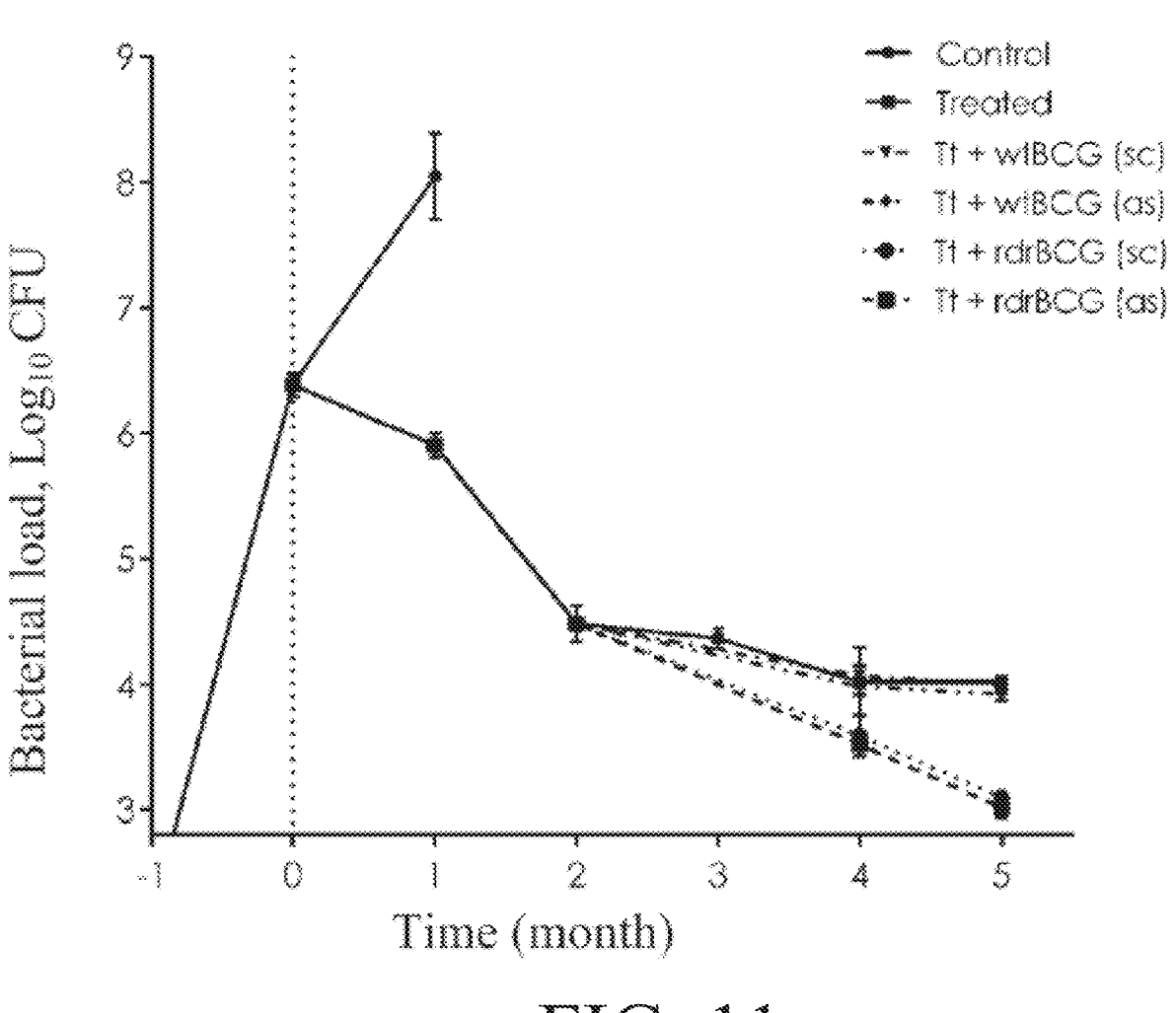
FIG. 11 shows a therapeutic effect of the recombinant drug-resistant BCG on the infection with rifampicin-resistant Mtb H37Rv.

The bacterial load detection results were shown in FIG. 11. It can be seen from the experimental results that, whether the immunization with the recombinant drug-resistant BCG strain is conducted through aerosol infection (as) or subcutaneous injection (sc), the recombinant drug-resistant BCG can continuously significantly reduce a bacterial load in the lung compared with the WT BCG treatment group, and thus has the potential and value to serve as a therapeutic BCG vaccine.

Finally, it should be noted that the above examples are provided merely to describe the technical solutions of the present disclosure, rather than to limit the protection scope of the present disclosure. Although the present disclosure is described in detail with reference to preferred examples, a person of ordinary skill in the art should understand that modifications or equivalent replacements may be made to the technical solutions of the present disclosure without departing from the spirit and scope of the technical solutions of the present disclosure.

The invention claimed is:

1. A drug-resistant *Bacillus* Calmette-Guerin (BCG) strain, wherein the drug-resistant BCG strain is a mutant strain of *Mycobacterium bovis* (*M. bovis*) BCG, and the drug-resistant BCG strain comprises the following gene mutations: 660G>A of embB gene, 417A>G or 216C>T of embC gene, 145G>A or 228T>C or 447A>C or 483C>T of Rv3806c gene, 128G>A of rpsL gene, 192delG of rrs gene, 448C>A of eis gene, 262G>A or 263G>A of gyrA gene, and 63T>C of ethA gene.

2. The drug-resistant BCG strain according to claim 1, wherein the drug-resistant BCG strain is named as drug-resistant BCG and is deposited in the Guangdong Microbial Culture Collection Center (GDMCC) located at Guangdong Institute of Microbiology, No. 100 Xianlie Middle Road Guangzhou, China, with an accession number of GDMCC 60969.

3. A construction method of a recombinant drug-resistant BCG strain, comprising transforming a plasmid carrying sequences of *Mycobacterium tuberculosis* (Mtb)-identifying protein-associated genes into the drug-resistant BCG strain according to claim 1, wherein the Mtb-identifying protein-associated genes are genes Ag85b and Rv2628.

4. A construction method of a recombinant drug-resistant BCG strain, comprising transforming a plasmid carrying sequences of Mtb-identifying protein-associated genes into the drug-resistant BCG strain according to claim 2, wherein the Mtb-identifying protein-associated genes are genes Ag85b and Rv2628.

5. A recombinant drug-resistant BCG strain obtained by the construction method according to claim 4.

6. A pharmaceutical composition for treating TB, comprising the recombinant drug-resistant BCG strain according to claim 5.

7. The pharmaceutical composition according to claim 6, further comprising at least one selected from the group consisting of ethambutol (EMB), levofloxacin (LFX), prothionamide (PRO), and amikacin (AMK).

* * * * *

SEQUENCE LISTING

```
Sequence total quantity: 46
SEQ ID NO: 1          moltype = DNA  length = 18
FEATURE               Location/Qualifiers
source                1..18
                      mol_type = other DNA
                      organism = synthetic construct
SEQUENCE: 1
cccaatgttc gccgctac                                       18

SEQ ID NO: 2          moltype = DNA  length = 18
FEATURE               Location/Qualifiers
source                1..18
                      mol_type = other DNA
                      organism = synthetic construct
SEQUENCE: 2
acgaggctcg atggtagg                                       18

SEQ ID NO: 3          moltype = DNA  length = 18
FEATURE               Location/Qualifiers
source                1..18
                      mol_type = other DNA
                      organism = synthetic construct
SEQUENCE: 3
gggatcggtg gagcagta                                       18

SEQ ID NO: 4          moltype = DNA  length = 18
FEATURE               Location/Qualifiers
source                1..18
                      mol_type = other DNA
                      organism = synthetic construct
SEQUENCE: 4
accgagcagc ataggagg                                       18

SEQ ID NO: 5          moltype = DNA  length = 18
FEATURE               Location/Qualifiers
source                1..18
                      mol_type = other DNA
                      organism = synthetic construct
```

15                                                                                        16

```
SEQUENCE: 5
gatgtggccg tgggtgtt                                                            18

SEQ ID NO: 6              moltype = DNA   length = 18
FEATURE                   Location/Qualifiers
source                    1..18
                          mol_type = other DNA
                          organism = synthetic construct
SEQUENCE: 6
cgtcaccgac agccacaa                                                            18

SEQ ID NO: 7              moltype = DNA   length = 19
FEATURE                   Location/Qualifiers
source                    1..19
                          mol_type = other DNA
                          organism = synthetic construct
SEQUENCE: 7
ttttccagga tggcgtagc                                                           19

SEQ ID NO: 8              moltype = DNA   length = 18
FEATURE                   Location/Qualifiers
source                    1..18
                          mol_type = other DNA
                          organism = synthetic construct
SEQUENCE: 8
ccgaccggat cgtcaaca                                                            18

SEQ ID NO: 9              moltype = DNA   length = 21
FEATURE                   Location/Qualifiers
source                    1..21
                          mol_type = other DNA
                          organism = synthetic construct
SEQUENCE: 9
cctggcagct tactacgtgt c                                                        21

SEQ ID NO: 10             moltype = DNA   length = 18
FEATURE                   Location/Qualifiers
source                    1..18
                          mol_type = other DNA
                          organism = synthetic construct
SEQUENCE: 10
cggcatcatc gtcgtctg                                                            18

SEQ ID NO: 11             moltype = DNA   length = 19
FEATURE                   Location/Qualifiers
source                    1..19
                          mol_type = other DNA
                          organism = synthetic construct
SEQUENCE: 11
tcacggcggt agaagagca                                                           19

SEQ ID NO: 12             moltype = DNA   length = 20
FEATURE                   Location/Qualifiers
source                    1..20
                          mol_type = other DNA
                          organism = synthetic construct
SEQUENCE: 12
ccacgcagat gtcgcaaaga                                                          20

SEQ ID NO: 13             moltype = DNA   length = 19
FEATURE                   Location/Qualifiers
source                    1..19
                          mol_type = other DNA
                          organism = synthetic construct
SEQUENCE: 13
tgcgaaagat ccaaccctc                                                           19

SEQ ID NO: 14             moltype = DNA   length = 21
FEATURE                   Location/Qualifiers
source                    1..21
                          mol_type = other DNA
                          organism = synthetic construct
SEQUENCE: 14
agaccaaccg tgtaggcaaa t                                                        21

SEQ ID NO: 15             moltype = DNA   length = 20
FEATURE                   Location/Qualifiers
source                    1..20
                          mol_type = other DNA
```

-continued

```
                        organism = synthetic construct
SEQUENCE: 15
acttggctcc gcacggctat                                                    20

SEQ ID NO: 16          moltype = DNA   length = 18
FEATURE                Location/Qualifiers
source                 1..18
                       mol_type = other DNA
                       organism = synthetic construct
SEQUENCE: 16
atccggcgac ggcattca                                                      18

SEQ ID NO: 17          moltype = DNA   length = 21
FEATURE                Location/Qualifiers
source                 1..21
                       mol_type = other DNA
                       organism = synthetic construct
SEQUENCE: 17
cgactggctc atatcgagaa t                                                  21

SEQ ID NO: 18          moltype = DNA   length = 20
FEATURE                Location/Qualifiers
source                 1..20
                       mol_type = other DNA
                       organism = synthetic construct
SEQUENCE: 18
aatacctgcg gatttcgtgt                                                    20

SEQ ID NO: 19          moltype = DNA   length = 18
FEATURE                Location/Qualifiers
source                 1..18
                       mol_type = other DNA
                       organism = synthetic construct
SEQUENCE: 19
gcgggcggaa acaagcaa                                                      18

SEQ ID NO: 20          moltype = DNA   length = 18
FEATURE                Location/Qualifiers
source                 1..18
                       mol_type = other DNA
                       organism = synthetic construct
SEQUENCE: 20
caaggcggtg ggacaaca                                                      18

SEQ ID NO: 21          moltype = DNA   length = 18
FEATURE                Location/Qualifiers
source                 1..18
                       mol_type = other DNA
                       organism = synthetic construct
SEQUENCE: 21
ccgcatcgcg tgatcctt                                                      18

SEQ ID NO: 22          moltype = DNA   length = 18
FEATURE                Location/Qualifiers
source                 1..18
                       mol_type = other DNA
                       organism = synthetic construct
SEQUENCE: 22
cgctgaccac gccgaaaa                                                      18

SEQ ID NO: 23          moltype = DNA   length = 18
FEATURE                Location/Qualifiers
source                 1..18
                       mol_type = other DNA
                       organism = synthetic construct
SEQUENCE: 23
tttccgaggc gcacgagg                                                      18

SEQ ID NO: 24          moltype = DNA   length = 18
FEATURE                Location/Qualifiers
source                 1..18
                       mol_type = other DNA
                       organism = synthetic construct
SEQUENCE: 24
cgtcgggagc cagatgca                                                      18

SEQ ID NO: 25          moltype = DNA   length = 25
FEATURE                Location/Qualifiers
source                 1..25
```

-continued

```
                              mol_type = other DNA
                              organism = synthetic construct
SEQUENCE: 25
ttcatatgac agacacgacg ttgcc                                    25

SEQ ID NO: 26          moltype = DNA   length = 26
FEATURE                Location/Qualifiers
source                 1..26
                       mol_type = other DNA
                       organism = synthetic construct
SEQUENCE: 26
cgcaagctta attgcccgtc tggtct                                   26

SEQ ID NO: 27          moltype = DNA   length = 17
FEATURE                Location/Qualifiers
source                 1..17
                       mol_type = other DNA
                       organism = synthetic construct
SEQUENCE: 27
ccgtatgccg gacgtcg                                             17

SEQ ID NO: 28          moltype = DNA   length = 15
FEATURE                Location/Qualifiers
source                 1..15
                       mol_type = other DNA
                       organism = synthetic construct
SEQUENCE: 28
gcggccgacg atcac                                               15

SEQ ID NO: 29          moltype = DNA   length = 18
FEATURE                Location/Qualifiers
source                 1..18
                       mol_type = other DNA
                       organism = synthetic construct
SEQUENCE: 29
gcggcttacg cctgatgt                                            18

SEQ ID NO: 30          moltype = DNA   length = 18
FEATURE                Location/Qualifiers
source                 1..18
                       mol_type = other DNA
                       organism = synthetic construct
SEQUENCE: 30
cagggcgggt ttgacatt                                            18

SEQ ID NO: 31          moltype = DNA   length = 21
FEATURE                Location/Qualifiers
source                 1..21
                       mol_type = other DNA
                       organism = synthetic construct
SEQUENCE: 31
tatctatgga tgaccgaacc t                                        21

SEQ ID NO: 32          moltype = DNA   length = 18
FEATURE                Location/Qualifiers
source                 1..18
                       mol_type = other DNA
                       organism = synthetic construct
SEQUENCE: 32
tgggacaaca cctggaac                                            18

SEQ ID NO: 33          moltype = DNA   length = 18
FEATURE                Location/Qualifiers
source                 1..18
                       mol_type = other DNA
                       organism = synthetic construct
SEQUENCE: 33
gcccgctggg tttgtttg                                            18

SEQ ID NO: 34          moltype = DNA   length = 25
FEATURE                Location/Qualifiers
source                 1..25
                       mol_type = other DNA
                       organism = synthetic construct
SEQUENCE: 34
gatgacaccc gatgtcgctt gagcc                                    25

SEQ ID NO: 35          moltype = DNA   length = 19
FEATURE                Location/Qualifiers
```

-continued

```
source                    1..19
                          mol_type = other DNA
                          organism = synthetic construct
SEQUENCE: 35
ggcgatcaaa gctccagtc                                                    19

SEQ ID NO: 36             moltype = DNA   length = 19
FEATURE                   Location/Qualifiers
source                    1..19
                          mol_type = other DNA
                          organism = synthetic construct
SEQUENCE: 36
cgaatccagc taccgcact                                                    19

SEQ ID NO: 37             moltype = DNA   length = 20
FEATURE                   Location/Qualifiers
source                    1..20
                          mol_type = other DNA
                          organism = synthetic construct
SEQUENCE: 37
tcgtggtgat cgaggctgag                                                   20

SEQ ID NO: 38             moltype = DNA   length = 19
FEATURE                   Location/Qualifiers
source                    1..19
                          mol_type = other DNA
                          organism = synthetic construct
SEQUENCE: 38
cggccaagtc gtcgctgtt                                                    19

SEQ ID NO: 39             moltype = DNA   length = 21
FEATURE                   Location/Qualifiers
source                    1..21
                          mol_type = other DNA
                          organism = synthetic construct
SEQUENCE: 39
ggctatgcac ttccgctctt t                                                 21

SEQ ID NO: 40             moltype = DNA   length = 18
FEATURE                   Location/Qualifiers
source                    1..18
                          mol_type = other DNA
                          organism = synthetic construct
SEQUENCE: 40
ttgccgcttc caactccc                                                     18

SEQ ID NO: 41             moltype = DNA   length = 31
FEATURE                   Location/Qualifiers
source                    1..31
                          mol_type = other DNA
                          organism = synthetic construct
SEQUENCE: 41
cgggatccat gagacgactt tgacgcccga a                                      31

SEQ ID NO: 42             moltype = DNA   length = 35
FEATURE                   Location/Qualifiers
source                    1..35
                          mol_type = other DNA
                          organism = synthetic construct
SEQUENCE: 42
cccctgcagg gatccttaga ccgcaacggc aatct                                  35

SEQ ID NO: 43             moltype = DNA   length = 32
FEATURE                   Location/Qualifiers
source                    1..32
                          mol_type = other DNA
                          organism = synthetic construct
SEQUENCE: 43
ggaattccat atgatgtcca cgcaacgacc ga                                     32

SEQ ID NO: 44             moltype = DNA   length = 35
FEATURE                   Location/Qualifiers
source                    1..35
                          mol_type = other DNA
                          organism = synthetic construct
SEQUENCE: 44
cccctgcagg gatccttaga ccgcaacggc aatct                                  35

SEQ ID NO: 45             moltype = DNA   length = 19
```

-continued

```
FEATURE                 Location/Qualifiers
source                  1..19
                        mol_type = other DNA
                        organism = synthetic construct
SEQUENCE: 45
cgatgtggtc ggataggca                                          19

SEQ ID NO: 46           moltype = DNA   length = 21
FEATURE                 Location/Qualifiers
source                  1..21
                        mol_type = other DNA
                        organism = synthetic construct
SEQUENCE: 46
actcacctgc ggtttatctg c                                       21
```